United States Patent [19]

Frenkel

[11] Patent Number: 5,552,285
[45] Date of Patent: Sep. 3, 1996

[54] IMMUNOASSAY METHODS, COMPOSITIONS AND KITS FOR ANTIBODIES TO OXIDIZED DNA BASES

[75] Inventor: Krystyna Frenkel, Woodmere, N.Y.

[73] Assignee: New York University, New York, N.Y.

[21] Appl. No.: 269,617

[22] Filed: Jul. 1, 1994

Related U.S. Application Data

[63] Continuation of Ser. No. 841,633, Feb. 27, 1992, abandoned, which is a continuation-in-part of Ser. No. 660,992, Feb. 27, 1991, abandoned.

[51] Int. Cl.[6] .................. C12Q 1/68; G01N 33/53; G01N 33/564; G01N 33/00; C07H 21/02
[52] U.S. Cl. .................. 435/7.1; 435/6; 435/7.92; 436/94; 436/508; 536/23.1
[58] Field of Search .................. 435/6, 7.92, 975, 435/7.1, 810, 975; 436/508, 94; 536/23.1; 935/76, 77, 78

[56] References Cited

U.S. PATENT DOCUMENTS

| | | | |
|---|---|---|---|
| 3,897,212 | 7/1975 | Leon et al. | 436/508 |
| 4,234,563 | 11/1980 | Rippe | 424/8 |
| 4,251,514 | 2/1981 | Rippe | 424/8 |
| 4,281,061 | 7/1981 | Zuk et al. | 435/7 |
| 4,493,899 | 1/1985 | Smith et al. | 436/508 |

FOREIGN PATENT DOCUMENTS

| | | | |
|---|---|---|---|
| 0205643 | 6/1985 | European Pat. Off. | 436/508 |

OTHER PUBLICATIONS

Kim et al; Proc Am. Ass. Cancer Research vol. 31, Mar. 1990 p. 147.
Erlanger et al; 1964, PNAS 52:68.
Munus et al., "Antibody–Nucleic Acid Complexes . . . Mice". Biochemistry 1984, 23, 2964–2970.
Leadon et al, 1983. Monoclonal Antibody to DNA Containg Thymineglycol. Mutation Research 112:191–200.
Degan, P. et al. 1991. Carcinogenesis, vol. 12 No. 5 pp. 865–871.
Tijsser, "Practice & Theory of Enzyme Immunoassuys", Elsevier, N.Y. 1985, pp. 308–3111.
Blount et al, FEBS Letters, 245(1–2):100–104, 1989.
Blount et al, Clin. Exp. Immunol., 81:384–389, 1990.
Blount et al, Clin Exp. Immunol, 81: 384–389, 1989.
Blount et al, FEBS Letters, 245(1–2) : 100–104, 1990.
Munns et al "a", Biochemistry 23:2458–2464, 1984.
Munn et al "b", Biochemistry 23:2964–2970, 1984.
Kim et al, Proc. Am. Assoc. Clnc. Res, 31:147, 1980.

*Primary Examiner*—James C. Housel
*Assistant Examiner*—Jennifer Shaver
*Attorney, Agent, or Firm*—Browdy & Neimark

[57] ABSTRACT

Compositions, immunoassay methods, and kits are provided for detecting antibodies specific for oxidized DNA bases, including diagnosis of inflammatory diseases and related conditions, as well as monitoring of the progress or therapy of such diseases and conditions.

23 Claims, 10 Drawing Sheets

IMMUNOASSAY METHODS, COMPOSITIONS AND KITS FOR ANTIBODIES TO OXIDIZED DNA BASES

CROSS-REFERENCE TO RELATED APPLICATIONS

This application is a continuation of application Ser. No. 07/841,633, filed Feb. 27, 1992, now abandoned, which was a CIP of application Ser. No. 07/660,992, filed Feb. 27, 1991, now abandoned.

BACKGROUND OF THE INVENTION

1. Field of the Invention

The invention relates immunoassay methods for detecting antibodies specific for oxidized DNA bases. Such methods are useful in the diagnosis and monitoring of inflammatory and autoimmune diseases.

2. Description of the Background Art

Chronic inflammation is known to be involved in a large number of diseases, including autoimmune diseases such as systemic lupus erythematosus (SLE) and rheumatoid arthritis (RA) as well as in cancer (J. C. Fantone et al., *Am. J. Pathol.* 07, 397 (1982); B. A. Freeman et al., *Lab Invest.* 47, 412 (1982); Y. Niwa et al., *Inflammation* 9, 163 (1985); C. E. Cross et al., *Ann, Int, Med,* 107, 526 (1987); S. Blount et al., *Clin. Exp. Immunol,* 81, 384 (1990)). In SLE, autoantibodies are produced which are directed against an array of nuclear antigens. Such antibodies, known as antinuclear antibodies or ANA, include antibodies reactive with the patient's own DNA. The ultimate stimulus for production of ANA and anti-DNA antibodies in these patients is not clear (B. D. Stollar, *Clinics in Immunology and Allergy* 1(2), 243 (1981); A. J. G. Swaak et al., *Ann. Rheum. Dis.* 40, 45 (1981); E. M. Tan et al., *Arthritis Rheum.* 25 (11.), 1271 (1982); T. Swaak et al., *Ann. Rheum. Dis.* 44, 245 (1985); D. S. Pisetsky et. al., Arthritis Rheum. 33(2), 153 (1990)).

Of the various serological markers, the presence of circulating antibodies reactive with double-stranded (ds) DNA seems to best correlate with the clinical manifestations of SLE. Complexes of DNA with anti-dsDNA antibodies are thought to precipitate in the renal glomeruli and result in glomerulo-nephritis (C. Bruneau et al., *J. clin. Invest.* 64, 191 (1979)). However, the factor or factors responsible for the release of DNA fragments from nuclear DNA is not yet known.

Oxidative stress contributes to the pathogenesis of a broad array of diseases, including autoimmune diseases, as described above, cardiac disease such as ischemia/reperfusion injury (Jolly, S. R. et al., *Circ. Res.* 34:277–285 (1984); McCord, J. M. *New Engl. J, Med.* 312:159–163 (1985), and neoplastic abnormalities (Vuillaume, M., *Murat, Res.* 1.86:43–72 (1987); Malins, D.C. et al., *Canc. Res.* 51:5430–5432 (1991)). Inflammatory conditions are associated with increased infiltration of phagocytic cells into reactive tissue sites. This infiltration is also accompanied by enhanced oxidant formation (J. A. Badewy et al., *Annu. Rev. Biochem.* 49, 695 (1980); S. J. Klebanoff, *Ann. Intern. Med.* 93, 480 (1980); B. M. Babior, *Blood* 64, 959 (1984); S. A. Weitzman et al., *Blood* 76, 655 (1990); P. Biemond et al., *J. Clin.* 73, 1576 (1984)). Phagocytic cells, in particular polymorphonuclear leukocytes (PMNs) or neutrophils, generate large amounts of active oxygen species when activated by a variety of stimuli including immune complexes or complement-derived fragments (Fantone et al., supra; Freeman et al., supra; Niwa et al., supra; Cross et al., supra; Badewy et al., supra; Klebanoff, supra; Babior, supra; Weitzman et al., supra; K. Frenkel, *Environ, Health Persp.* 81, 45 (1989); K. T. Oldham et al., *Free Rad. Biol. Med.* 4, 387 (1988)). Chronic inflammation increases the incidence of autoimmune disease and cancer (Cross et al., supra; vuillaume, supra). ulcerative coliris may progress to colon cancer, while pulmonary infiltration and activation of PMNs and alveolar macrophages are factors in the pathogenesis of lung cancer (Cross et al., supra).

The reactive oxygen species include superoxide anion radicals that dismutate either spontaneously or enzymatically to hydrogen peroxide ($H_2O_2$) (K. Frenkel, supra). Peroxide has been shown to activate the complement pathway in the presence of Fe or Cu ions (M. Shingu et al., *Dermatologica* 179 (Suppl. 1), 107 (1989)). Furthermore, it is $H_2O_2$ that traverses cellular and nuclear membranes almost like water, and reaches the nuclear DNA (K. Frenkel, supra; R. Meneghini, *Mutation Res.* 195, 215 (1988); B. Halliwell et al., *Arch. Biochip. Biophys.* 246, 501 (1986); M. Chevion, *Free Rad. Biol. Med.* 5, 27 (1988)). Once in the nucleus, $H_2O_2$ reacts at sites that contain bound Fe or Cu, leading to the formation of hydroxyl radical (.OH)-like species that cause site-specific damage to DNA. Indeed, $H_2O_2$ generated by a number of cellular processes is known to cause DNA strand breaks and to oxidize DNA bases. Products of this oxidation include 5-hydroxymethyl uracil (HMU), thymine glycol (TG) and 8-hydroxyguanine (8-OHG) (Frenkel, supra; D. R. Dutton et al., Carcinogenesis 6:1279 (1985); K. Frenkel et al., *Cancer Res,* 46, 5533 (1986); K. Frenkel et al., *Carcinogenesis* 8, 455 (1987); K. Frenkel et al., in: *Oxy-Radicals in Molecular Biology and Pathology*, P. A. Cerutti et al., Eds., Alan R. Liss, Inc., New York, N.Y., 1988, pp. 509–524; K. Frenkel et al., *Free Rad. Biol. Med.* 9(Suppl. 1), 170 (1990); H. Kasai et al., *Carcinogenesis* 7, 1849 (1986); E. S. Fiala et al., *Cancer Res.* 49, 5518 (1989); S. A. Leadon, *Brit. J. Cancer* 55(Suppl. 8), 113 (1987); J. G. Lewis et al., *Cancer Res.* 45:1270 (1985); J. H. Jackson et. al., *J. Clin Invest.* 84, 1644 (1989); K. S. Kasprzak et al., Carcinogenesis. 11, 647 (1990)).

Sera of SLE patients may contain increased amounts of catalase (M. Shingu et al., supra); this enhancement is characteristic of oxidative stress (G. Storz et al., TIG 6(11), 363 (1990)).

Rabbit polyclonal antibodies specific for the oxidized base thymine glycol have been described (Rajagopalan et., *Radiat. Res.* 97:499–510 (1984)). Monoclonal antibodies specific for thymine glycol have been produced and used to detect thymine glycol in oxidized DNA by ELISA (Leadon, S. A. et al., *Mutat. Res.* 112:191–200 (1983); Kaneko, M. et al., *Canc, Res.* 46:71–75 (1986); Leadon, S. A., *Brit. J. Canc.* 55 (Suppl VIII):113–167 (1987); Hubbard, K. et al., *Radiat. Res.* 118:257–268 (1989)). In all of these studies, the antibody was produced as a reagent for the purpose of identifying oxidative damage to DNA in immunoassays as an improvement over enzymatic and other biochemical assays to detect such alterations. Thus, the assays always involved whole DNA or polynucleotides as the analyte.

Because the previous work on thymine glycol antibodies was intended to provide an assay for the presence of the modified base in DNA, a useful assay in which the analyte is the antibody specific for an oxidized DNA base has not been previously contemplated and is not currently available. The ability to measure such antibodies would be of great value for early diagnosis of inflammatory conditions associated with oxidative damage, and for monitoring the progress of such conditions and their response to therapy.

For example, Djuric et al. (*J. Nat'l. Canc., Inst*, 83:766–769 (1991)) found a positive correlation between fat intake and the presence of HMU in white blood cells of women at high risk for breast cancer. The methods and compositions of the present invention would be useful to monitor such high risk individuals for oxidative damage prior to the onset of frank neoplastic disease.

Caruthers et al. (U.S. Pat. No. 4,458,066) discloses nucleotides covalently bound to an inorganic polymer support, for the synthesis of oligonucleotide chains. Caruthers et al. does not suggest the use of nucleotides containing oxidized bases. Importantly, the methods disclosed would not be useful with oxidized bases because reactive groups (e.g., alcohols) on the oxidized base's ring structure would interfere in the covalent attachment via the sugar moiety to the inorganic polymer. Furthermore, Caruthers et al. does not suggest the use of nucleosides "artificially polymerized" by binding to a carrier such as a protein, wherein the carrier is then non-covalently attached to a solid support. Furthermore, Caruthers et al. only envisions inorganic supports.

SUMMARY OF THE INVENTION

The present inventors conceived of the notion that chronic enhanced production of oxidants in SLE or other disease states, particularly chronic inflammation, causes formation of strand breaks in DNA and oxidation of DNA bases at levels that exceed the antioxidant and DNA repair capacities of the cells. The released fragments of damaged DNA and, in particular, oxidized bases present in those fragments can serve as antigenic determinants, and induce the production of autoantibodies which react with the DNA that contains such bases. The present inventors showed that sera of patients suspected of having SLE or other inflammatory diseases contained antibodies that recognized oxidized DNA bases. This serves as the basis of a novel composition and immunoassay for detecting these antibodies. Such assays are useful in diagnosis and prognosis of inflammatory conditions, as well as any other conditions including neoplasia, as well as potentially damaging exposure to ionizing or UV irradiation, or cancer chemotherapy drugs, which result in oxidative DNA damage.

The present invention is thus directed to a composition useful for detecting or measuring antibodies specific for an oxidized DNA base, comprising a nucleoside or nucleotide containing an oxidized base immobilized on a solid phase support, wherein the base is not part of an oligonucleotide or polynucleotide molecule.

In a preferred embodiment, the nucleoside or nucleotide containing the oxidized base is covalently linked to a protein which is immobilized on the support. Non-human proteins, such as bovine serum albumin, human serum albumin, ovalbumin or milk protein, are preferred when the composition is to be used for assaying human antibodies.

Oxidized DNA bases useful for the compositions and methods of the present invention include 5-hydroxymethyl uracil, thymine glycol and 8-hydroxyguanine.

Any of a number of support materials are useful for immobilizing the oxidized DNA base according to the present invention, including glass, polystyrene, polypropylene, polyethylene, dextran, nylon, amylases, natural and modified celluloses, polyacrylamide, agarose, and magnetite. A preferred support is polystyrene, preferably in the form of a microtiter plate.

The present invention is also directed to an immunoassay method for detecting the presence or measuring the concentration of an antibody specific for an oxidized DNA base, comprising contacting a sample suspected of containing such an antibody with a nucleotide or nucleoside containing the oxidized base, wherein the base is not part of an oligonucleotide or polynucleotide molecule, and measuring the amount of antibody in the sample which is specific for the oxidized base, thereby detecting or measuring the antibody.

In one embodiment, the immunoassay method comprises:

(a) contacting a sample suspected of containing the antibody with a composition as described above; (b) allowing antibodies in the sample to bind to the oxidized base; (c) adding a detectably labeled binding partner for the antibody to the bound antibodies and allowing the binding partner to bind to the antibodies; and (d) measuring the amount of bound or unbound labeled binding partner, thereby detecting or measuring the antibody.

Preferably, in the immunoassay method, the nucleoside or nucleotide containing the oxidized base is covalently linked to a protein which is immobilized on the support.

Preferred binding partners in the above immunoassay method include an antibody specific for a human immunoglobulin and a bacterial protein capable of binding to a human immunoglobulin molecule. A preferred detectable label for the above immunoassay method is an enzyme.

The present invention is further directed to a method of diagnosing an inflammatory or neoplastic disease or condition in a subject comprising obtaining from the subject a sample of a biological fluid and detecting the presence of antibodies specific for an oxidized DNA base using a method as described above, wherein the presence of the antibodies indicates that the inflammatory disease or condition exists.

The present invention also includes a method of monitoring the progression or the regression of an inflammatory disease or condition in a subject comprising obtaining from the subject on at least two occasions separated in time by at least seven days a first and a second sample of a biological fluid and measuring in each sample the concentration of antibodies specific for an oxidized DNA base using a method as described above, wherein an increase in the concentration of the antibodies from the first sample to the second sample is associated with progression of the disease or condition and wherein a decrease in the concentration of the antibodies from the first sample to the second sample is associated with regression of the disease or condition.

Also included in the present invention is a kit for detecting the presence or measuring the concentration of antibodies specific for an oxidized DNA base, the kit being compartmentalized to receive in close confinement one or more containers, the kit comprising: (a) a first container containing a nucleoside or nucleotide containing the oxidized base, immobilized on, or capable of being immobilized on, a solid phase support; and (b) instructions for performing an immunoassay as described above.

The above kit may additionally comprise: (c) a second container containing a detectably labeled binding partner for the antibodies.

The above kit may additionally comprise: (d) a third container containing an agent capable of reacting with the detectably labeled binding partner to yield a detectable reaction product.

A preferably binding partner for the above kit is (a) an antibody specific for a human immunoglobulin or (b) a bacterial protein capable of binding to a human immunoglobulin molecule.

In a preferred kit embodiment, the detectable label is selected from the group consisting of an enzyme, a radionuclide, a fluorescent label, a chemiluminescent label and a bioluminescent label.

Preferred enzyme labels include malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase.

DESCRIPTION OF THE PREFERRED EMBODIMENTS

Figure 1:
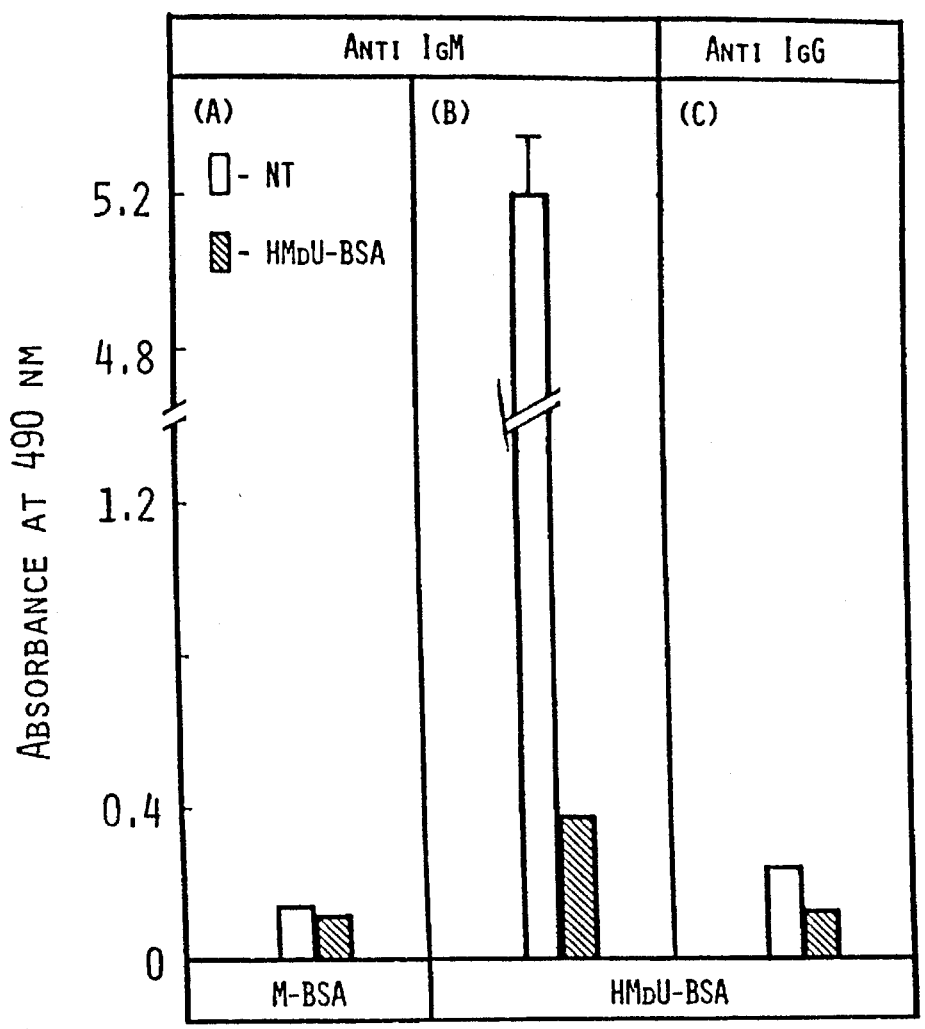
FIG. 1 is a graph showing specific binding to 5-hydroxymethyl-2'-deoxyuridine coupled to bovine serum albumin (HMdU-BSA) and non-specific binding to mock-coupled bovine serum albumin (M-BSA) of antibodies present in ANA$^+$ serum of a lupus patient, and recognition of these antibodies by goat anti-human IgM, but not by anti-IgG, as determined by ELISA. Serum #5 (2.5K dilution; 1 ml) was incubated in the absence (NT) or presence of 800 µg HMdU-BSA at 37° C. for 1 h, then an aliquot was applied to plates coated with M-BSA (Panel A) or HMdU-BSA (Panels B and C). After incubation at 37° C. for 2 h, anti-human IgM (Panels A and B) or anti-IgG (Panel C) was added, followed by incubation with the substrate.

In the following description, reference will be made to various methodologies known to those skilled in the art of immunology. Publications and other materials setting forth such known methodologies to which reference is made are entirely incorporated herein by reference. Standard reference works setting forth the general principles of immunology include Roitt, I., *Essential Immunology*, 6th Ed., Blackwell Scientific Publications, Oxford (1988); Roitt, I. et al., Immunology, C. V. Mosby Co., St. Louis, Mo. (1985); Klein, J., Immunology, Blackwell Scientific Publications, Inc., Cambridge, Mass., (1990); Klein, J., Immunology: The Science of Self-Nonself Discrimination, John Wiley & Sons, New York, N.Y. (1982)); Kennett, R., et al.,; and Eisen, H. N., (In: *Microbiology*, 3rd Ed. (Davis, B. D., et al., Harper & Row, Philadelphia (1980)); Paterson, P.Y., *Textbook of Immunopathology* (Mischer et al., eds.), Grune and Stratton, New York, pp. 179–213 (1986). A standard work setting forth details of monoclonal antibody production and characterization, and immunoassay procedures, is Hartlow, E. et al., *Antibodies: A Laboratory Manual*, Cold Spring Harbor Laboratory Press, Cold Spring Harbor, N.Y., 1988.

An immunoassay for antibodies specific for oxidized DNA bases typically comprises incubating a biological sample from a subject suspected of having a condition associated with such antibodies in the presence of an "antigen containing reagent" which includes an oxidized base, and detecting the binding to the oxidized base of the antibody which is in the sample.

DNA bases include the pyrimidine bases thymine (also known as 5-methyl uracil), cytosine, and 5-methyl cytosine, and the purine bases adenine and guanine. Preferably, the oxidized form of these basis is used according to the present invention in the form of a deoxyribonucleoside, containing the sugar deoxyribose, or a deoxyribonucleotide, containing deoxyribose and phosphate.

Preferred oxidized DNA bases useful for the compositions and methods of the present invention include 5-hydroxymethyl uracil (which is oxidized thymine), thymine glycol and 8-hydroxyguanine. However, dozens of other oxidized DNA bases formed by oxidation of DNA are known in the art (R. Teoule, *Int. J. Radiatio Biol.* 51:573–589 (1987); G. W. Teebor et al., *Int. J. Radiation Biol*, 54:131–150 (1988), which references are hereby entirely incorporated by reference). The oxidation relative to the native DNA base is generally associated with a substituent of the purine or pyrimidine ring structure, for example oxidation of the methyl group to hydroxymethyl in the conversion of thymine to HMU. Thus, as intended herein, the oxidation is in the base, and not in the sugar or phosphate portion of the nucleoside or nucleotide.

The oxidized bases may either be obtained commercially or synthesized chemically using methods well known in the art and are preferably used in the form of a nucleoside or nucleotide to allow conjugation to a carrier molecule, preferably a protein. While use of 5-hydroxymethyl uracil is exemplified in particular detail herein, any of these oxidized bases may be used according to the teachings of the present invention.

Provided below are preferred methods for synthesis of cis-thymidine glycol (also known as 5,6-dihydroxy-5,6-dihydrothymidine) monophosphate, pdTG), 8hydroxyguanosine (8-OHrG) and 8-hydroxy-2'-deoxyguanosine monophosphate (8-OHdGMP) and methods for their coupling to BSA. cis-Thymine glycol, thymidine glycol and its monophosphate are commonly synthesized through formation of bromohydrins or by $OsO_4$ oxidation (Leadon et al., 1983 supra; Rajagopalan et al., supra). Preferably, the synthesis involves $KMnO_4$ as an oxidizing agent following a procedure of Iida et al. (BioGhim. Biophys Acta 213:1–13 (1970)) as modified by Frenkel et al. (*Biochemistry* 20:750–754 (1981); *Biochemistry* 20:7566–7571 (1981)). This method allows separation of the (+) isomer from the (−) isomer of pdTG and separate coupling of each isomer to BSA, which is advantageous in finding which isomer is formed in vivo. dTMP is oxidized with ice-cold $KMnO_4$ for 5 min. and the unreacted $KMnO_4$ is reduced with m-bisulfite. After removing the precipitate and concentrating, the mixture is chromatographed on Sephadex LH-20, a reverse-phase adsorbent for column chromatography, and the pdTG separated from unreacted dTMP. After precipitation of salts with ethanol and concentration, the two isomers are separated by HPLC (ODS, 1×25 cm) using ammonium acetate as eluent. To prove that the products are pdTG, the same synthesis may be carried out with [$^3$H]dTMP. Samples of putative [$^3$H] pdTG are treated with alkaline phosphatase and analyzed by HPLC; both pdTG isomers can be shown to release dTG. Both pdTG isomers are separately crystallized from methanol-isopropanol.

For coupling of pdTG to BSA, a neutral pH method is preferred. The periodate coupling method (Erlanger, B. et al., *Proc. Natl. Acad. Sci.* 3:68 (1964)) requires alkaline conditions, under which the thymine glycol ring is unstable. Using the neutral pH method, the isomers of cis-pdTG are separately coupled to BSA according to Hamagishi et al. (*J. Biochem.* 88:1785–1792)) using 1-ethyl-3-(3-dimethylaminopropyl) carbodiimide (EDCI) as a coupling agent. The products of coupling, designated as pdTG-1/BSA (I) and pdTG-2/BSA (II), are separated from free pdTG by passing the preparations through desairing gel (BioRad P6-DG) columns. The same method is used for preparation and purification of p[$^3$H]dTG/BSA I and II. Dialysis of p[$^3$H] dTG/BSA I and II showed that only a very small fraction of tritium was released, thus proving that virtually all radioactivity is bound to BSA. Samples of the $^3$H-containing conjugates were treated with 0.1N HCl at room temperature overnight and analyzed by HPLC. No free dTG was found under these conditions. Treatment of acid hydrosylates with alkaline phosphatase released [$^3$H]dTG from both isomer preparations, which demonstrates that dTG was coupled to BSA through the phosphate moiety. The content of conjugates may be established by UV spectrophotometry and specific activity. For example, conjugates I and II have been found to contain 27 nmol pdTG-1/nmol BSA and 24 nmol pdTG-2/nmol BSA, respectively. Conjugates of ovalbumin have been found to contain lower levels of substitution than BSA. Conjugates may be lyophilized and stored at −20° C.

Coupling of guanosine (rG) to BSA was described by Erlanger et al. (supra), where periodate oxidation was followed by borohydride reduction under alkaline conditions, resulting in 2'-deoxyguanosine (dG) being coupled to BSA. Coupling of 8-OHrG to BSA under these conditions may result in some ring opening; however such open ring products are known to be generated in vivo as well. Hence, such open ring products may provide additional useful antigenic determinants for analysis of human sera according to the present invention. In one embodiment, 8-OHrG may be synthesized by treating 8-bromoguanosine dissolved in acetic acid with a 10-fold excess of freshly fused sodium acetate at 118° C. for 3 hrs (Ikehara, M. et al., *Chem. Pharm Bull.* 13:1140–1142 (1965)). Results using 8-bromoguanosine (commercially available) show that less acetate and lower temperature (70°–80° C.) are sufficient for removal of bromine and substitution by the hydroxyl group. After cooling, the mixed-bed ion exchange beads are added to the mixture, the mixture is filtered, and the beads washed with water. HPLC analysis (ODS, 1×25 cm) shows the presence of several products eluting before and after 8-bromoguanosine, which have the same UV spectra as the authentic 8-OHrG marker synthesized in Dr. Fiala's laboratory (American Health Foundation, Valhalla, N.Y.). That marker was synthesized using light-sensitization of methylene blue as a source of singlet oxygen. (While the latter method is good, the yield of 8-OHrG is very low). In method described above, the early-eluting peak co-chromatographed with the 8-OHrG marker. Products are separated into two fractions, early- and late-eluting from HPLC, and both are separately coupled to BSA according to Erlanger et al. (supra). This method is based on periodate oxidation of guanosine, followed by addition of BSA and reduction of the BSA complex with borohydride at alkaline pH. Coupling of 8-OHrG to protein using this method has been reported (Degan, P. et al., *Carcinogenesis* 12:865–871 (1991)), though no analysis of the product was performed. It is therefore uncertain whether the imidazole ring remains intact or is opened under these conditions. Furthermore, the 8-OHrG used by Degan et al., was synthesized by a different method than that described herein.

To be certain that the BSA conjugate contains intact 8-OHdG moieties, the coupling may be performed using EDCI, as described above for pdTG. 8-OHdGMP is synthesized from dGMP by oxidation with either (1) the Udenfriend reagent consisting of $FeSO_4$/EDTA and ascorbic acid with oxygen passing through the reaction mixture, or (2) $H_2O_2$ in the presence of ascorbate; both at pH 6.8, as described by Kasai et al. (*Nucleic Acids Res.* 12:2137–2145

(1984)) and Frenkel et al. (*Anal. Biochem*, 196:126–136 (1991)).

In a preferred embodiment of this invention, the oxidized DNA base-containing composition is an oxidized base-containing nucleoside or nucleotide conjugated to a protein. It is preferred that the protein be of a species other than that of the species being tested. For example, for assay of human antibodies specific for an oxidized DNA base, a non-human protein such as bovine serum albumin is preferred. One reason for this is the probability that, in a subject with autoimmunity or chronic inflammation, autoimmune antibodies including those specific for human albumin may be present and result in false positive results. Thus, for example, for assay of bovine antibodies, human serum albumin would be used. One of ordinary skill in the art will be able to determine which protein is appropriate or desirable for the particular assay application without undue experimentation, such as horse serum, ovalbumin or large proteins in non-fat dry milk.

In a preferred embodiment, the oxidized DNA base bound to a carrier molecule such as a protein, is brought in contact with, and allowed to bind or adhere to, a solid support (or carrier), such as nitrocellulose or polystyrene. This immobilized form of the oxidized base antigen is then allowed to interact with a biological sample, such that any specific antibodies in the sample will bind to the immobilized antigen. The support may then be washed with suitable buffers followed by treatment with a detectably labeled binding partner for the antibody.

A preferred binding partner is an anti-immunoglobulin antibody produced in a different species. Thus to detect a human antibody, for example, "second antibody," for example, a goat anti-human immunoglobulin antibody which is detectably labeled may be used. The solid phase support may then be washed with the buffer to remove unbound antibody. The amount of bound label on said solid support may then be detected by conventional means appropriate to the type of label used (see below).

Such a "second antibody" may be specific for a particular human immunoglobulin isotype, for example IgM, IgG1, IgG2, and the like, thus permitting identification of the isotype or isotypes of antibodies in the sample which are specific for the oxidized base. Alternatively, the second antibody may be specific for an idiotype of the sample antibody.

As alternatives to antibodies as binding partners for the sample antibody being detected, other known binding partners for human immunoglobulins, such as the staphylococcal protein A or streptococcal protein G, well-known in the art, may be used.

In another embodiment of this invention, a biological sample suspected of containing an antibody specific for an oxidized base may be treated with a solid support or carrier which is capable of immobilizing soluble proteins. The support may then be washed with suitable buffers followed by treatment with the oxidized base reagent, which may be detectably labeled. If the oxidized base reagent is not detectably labeled, a second reagent containing a detectably labeled binding partner for the oxidized base reagent is provided to the complex. The solid phase support may then be washed with the buffer to remove unbound antibody. The amount of bound label on said solid support may then be detected by conventional means. Possible binding partners for the oxidized base reagent include antibodies, for example monoclonal antibodies (mAb) specific for the oxidized base or the complex of the oxidized base with any structure to which it is bound such as a protein substituted with oxidized bases. Another type of binding partner may be a mAb specific for an epitope of a non-human protein portion of a protein-oxidized base complex.

By "solid phase support" is intended any support capable of binding antigen or antibodies or other binding partners according to the present invention. Well-known supports, or carriers, include glass, polystyrene, polypropylene, polyethylene, dextran, nylon, amylases, natural and modified celluloses, polyacrylamides, agaroses, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads, 96-well polystyrene microplates and test strips, all well-known in the art. Those skilled in the art will know many other suitable carriers for binding antibody or antigen, or will be able to ascertain the same by use of routine experimentation.

Using any of the assays described herein, those skilled in the art will be able to determine operative and optimal assay conditions for each determination by employing routine experimentation. Furthermore, other steps as washing, stirring, shaking, filtering and the like may be added to the assays as is customary or necessary for the particular situation.

A preferred type of assay to detect an antibody specific for an oxidized base according to the present invention is an enzyme immunoassay (EIA), or enzyme-linked immunosorbent assay (ELISA). In such assays, the detectable label bound to either an antibody-binding or antigen-binding reagent is an enzyme. This enzyme, in turn, when later exposed to its substrate, will react with the substrate in such a manner as to produce a chemical moiety which can be detected, for example, by spectrophotometric, fluorometric or by visual means. Enzymes which can be used to detectably label the reagents useful in the present invention include, but are not limited to, malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. For description of EIA procedures, see, for example, Engvall et al., *Immunochem.* 8:871 (1971); Van Weeman et al., *FEBS Lett.* 15:232 (1971); Voller, A., "The Enzyme Linked Immunosorbent Assay (ELISA)", *Diagnostic Horizons* 2:1–7, 1978)) (Microbiological Associates Quarterly Publication, Walkersville, Md.); Voller, A. et al., *Bull. WHO* 53:55–65 (1976); Voller, A. et al., *J. Clin. Pathol.* 31:507–520 (1978); Butler, J. E., *Meth. Enzymol.* 73:482–523 (1981); or Maggio, E. (ed.), *Enzyme Immunoassay*, CRC Press, Boca Raton, Fla., 1980.

In another embodiment, the detectable label may be a radiolabel, and the assay thus used termed a radioimmunoassay (RIA), which is well known in the art. See, for example, Yalow, R. et al., *Nature* 184:1648 (1959); Work, T. S., et al., *Laboratory Techniques in Biochemistry and Molecular Biology*, North Holland Publishing Company, N.Y., 1978, entirely incorporated by reference herein. The radioactive isotope can be detected by such means as the use of a gamma counter or a scintillation counter or by autoradiography. Isotopes which are particularly useful for the purpose of the present invention are: $^{3}H$, $^{125}I$, $^{131}I$, $^{35}S$, $^{14}C$, and preferably $^{125}I$.

It is also possible to label the antigen or antibody reagents useful in the present invention with a fluorescent compound. When the fluorescently labeled antibody is exposed to light of the proper wavelength, its presence can then be detected due to fluorescence. Among the most commonly used fluorescent labeling compounds are fluorescein isothiocyanate, rhodamine, phycoerythrin, phycocyanin, allophycocyanin, O-phthaldehyde and fluorescamine. The reagents can also be detectably labeled using fluorescence emitting metals such as $^{152}Eu$, or others of the lanthanide series. These metals can be attached to an antibody using such metal chelating groups as diethylenetriaminepentaacetic acid (DTPA) or ethylenediaminetetraacetic acid (EDTA).

The antigen or antibody reagents useful in the present invention also can be detectably labeled by coupling to a chemiluminescent compound. The presence of a chemiluminescent-tagged antibody or antigen is then determined by detecting the presence of luminescence that arises during the course of a chemical reaction. Examples of particularly useful chemiluminescent labeling compounds are luminol, isoluminol, acridinium ester, imidazole, acridinium salt and oxalate ester.

Likewise, a bioluminescent compound may be used to label the antigen or antibody reagents useful in the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Detection of the detectably labeled reagent according to the present invention may be accomplished by a scintillation counter, for example, if the detectable label is a radioactive gamma emitter, or by a fluorometer or colorimater for example, if the label is a fluorescent material. In the case of an enzyme label, the detection can be accomplished by colorimetric methods which employ a substrate for the enzyme. Detection may also be accomplished by visual comparison of the extent of enzymatic reaction of a substrate in comparison with similarly prepared standards.

For the purposes of the present invention, the antibody specific for an oxidized DNA base which is detected by the assay of this invention may be present in a biological sample. Any sample containing such an antibody can be used. However, one of the benefits of the present diagnostic invention is that invasive tissue removal may be avoided. Therefore, preferably, the sample is a biological solution such as, for example, blood, serum, saliva, urine, cerebrospinal fluid, amniotic fluid, lymph and the like. However, the invention is not limited to assays using only these samples, it being possible for one of ordinary skill in the art to determine suitable conditions which allow the use of other samples.

The binding molecules useful in the methods of the present invention may be adapted for utilization in an immunometric assay, also known as a "two-site" or "sandwich" assay. In a typical immunometric assay, a quantity of unlabeled antibody (or fragment of antibody) is bound to a solid support that is insoluble in the fluid being tested (i.e., blood, CSF, amniotic fluid, tissue homogenate, etc.) and a quantity of detectably labeled soluble antibody is added to permit detection and/or quantitation of the ternary complex formed between solidphase antibody, antigen, and labeled antibody.

Typical, and preferred, immunometric assays include "forward" assays in which the antibody bound to the solid phase is first contacted with the sample being tested to extract the antigen from the sample by formation of a binary solid phase antibody-antigen complex. After a suitable incubation period, the solid support is washed to remove the residue of the fluid sample, including unreacted antigen, if any, and then contacted with the solution containing an unknown quantity of labeled antibody (which functions as a "reporter molecule"). After a second incubation period to permit the labeled antibody to complex with the antigen bound to the solid support through the unlabeled antibody, the solid support is washed a second time to remove the unreacted labeled antibody. This type of forward sandwich assay may be a simple "yes/no" assay to determine whether antigen is present or may be made quantitative by comparing the measure of labeled antibody with that obtained for a standard sample containing known quantities of antigen. Such "two-site" or "sandwich" assays are described by Wide, *Radioimmune Assay Method*, Kirkham et al., Eds., E. & S. Livingstone, Edinburgh, 1970, pp 199–206.

In another type of "sandwich" assay, which may also be useful with the antigens of the present invention, the so-called "simultaneous" and "reverse" assays are used. A simultaneous assay involves a single incubation step as the antibody bound to the solid support and labeled antibody are both added to the sample being tested at the same time. After the incubation is completed, the solid support is washed to remove the residue of fluid sample and uncomplexed labeled antibody. The presence of labeled antibody associated with the solid support is then determined as it would be in a conventional "forward" sandwich assay.

In the "reverse" assay, stepwise addition first of a solution of labeled antibody to the fluid sample followed by the addition of unlabeled antibody bound to a solid support after a suitable incubation period is utilized. After a second incubation, the solid phase is washed in conventional fashion to free it of the residue of the sample being tested and the solution of unreacted labeled antibody. The determination of labeled antibody associated with a solid support is then determined as in the "simultaneous" and "forward" assays.

An alternative to the RIA and EIA is provided by various types of agglutination assays. Both direct and indirect agglutination immunoassays are well known in the art. In these assays, the agglutination of particles to which an antigen or an antibody is bound is used to indicate the presence or absence of the corresponding antibody or antigen. A variety of particles, including particles of latex, charcoal, kaolinire, or bentonite, as well as microbial cells or red blood cells, may be used as agglutinable carriers (Mochida, U.S. Pat. No. 4,308,026; Gupta et al., *J. Immunol. Meth.* 80:177–187 (1985); Castelan et al., *J. Clin. Pathol.* 21:638 (1968); Singer et al. (*Amer. J. Med.* [1956 (Dec)]: 888); Molinaro, U.S. Pat. No. 4,130,634). Such assays may be impeded by the problem of nonspecific agglutination of erythrocytes by anti-erythrocyte antibodies present in the sample being tested. This may be overcome by eliminating (or hiding) all naturally occurring antigenic sites on the particle by coating the particle with protein (Czismas (U.S. Pat. No. 3,639,558). Traditional hemagglutination assays are generally faster, but much less sensitive than RIA or EIA.

In addition to detection of antibodies, the present invention provides methods to detect and enumerate cells secreting an antibody specific for an oxidized DNA base. Thus, for example, any of a number of plaque or spot assays may be used. In such assays, a sample containing lymphoid cells, such as peripheral blood lymphocytes, is mixed with a reagent containing the antigen of interest. As the antibody secreting cells of the sample secrete their antibodies, the antibodies react with the antigen, and the reaction is visualized in such a way that the number of antibody secreting cells (or plaque forming cells) may be determined. The antigen, such as oxidized DNA bases in the present invention, may be coupled to indicator particles, such as erythrocytes, preferably sheep erythrocytes, arranged in a layer. As antibodies are secreted from a single cell, they attach to the surrounding antigenobearing erythrocytes. By adding complement components, lysis of the erythrocytes to which the antibodies have attached is achieved, resulting in a "hole" or "plaque" in the erythrocyte layer. Each plaque corresponds to a single antibody-secreting cell.

In a different embodiment, the sample containing antibody-secreting cells is added to a surface coated with an antigen-bearing reagent, for example, an oxidized DNA base conjugated to bovine serum albumin, attached to polystyrene. After the cells are allowed to secrete the antibody which binds to the immobilized antigen, the cells are gently washed away. The presence of a colored "spot" of bound antibody, surrounding the site where the cell had been, can be revealed using modified EIA or other staining methods well-known in the art. (See, for example, Sedgwick, J. D. et al., *J. Immunol. Meth.* 57:301–309 (1983); Czerkinsky, C. C. et al., *J. Immunol. Meth.* 65:109–121 (1983); Logtenberg, T. et. al., *Immunol. Lett.* 9:343–347 (1985); Walker, A. G. et al., *J. Immunol. Meth.* 104:281–283 (1987), which references are entirely hereby incorporated by reference.)

A number of inflammatory autoimmune diseases that show positive results in the ELISA according to the present invention are known to be associated with IgM antibodies reactive with DNA, in addition to or instead of antibodies reactive with DNA, as determined by IIF and other assays (J.-C. Bystryn, *Prog. Dematol.* 19:1 (1985); M. Gripenberg et al., *J. Immunol. Meth.* 62, 315 (1983); Y. Shoenfeld et al., N. Engl. *J. Med.* 308, 414 (1983); R. P. Taylor et al., Arthritis Rheum. 30, 176 (1987)). Moreover, IgA antibodies specific for oxidized dsDNA have been found in SLE (Blount et al., supra).

The compositions and methods of the present invention are useful for detecting antibodies to oxidized DNA bases in any of a number of conditions wherein oxidative damage occurs. In addition to the various autoimmune and inflammatory conditions and diseases, neoplastic diseases, or diabetes type I, where free radical production may occur, such oxidative damage is known to occur in response to a number of exogenous stimuli. For example, prolonged exposure to ionizing radiation, UV-irradiation, or cancer chemotherapeutic agents, such as adriamycin and bleomycin, is known to be associated with oxidative damage. Thus, individuals undergoing such exposure, for example as part of a cancer therapy regimen, a phototherapy regimen for skin disease (such as with the psoralens), or due to accidental exposure to low level radiation from nuclear power plants or the testing of nuclear devices, may respond to the production of oxidized DNA bases by developing antibodies to these bases.

The compositions and methods of the present invention, in particular the immunoassay methods, are useful for monitoring such individuals for the presence of such antibodies. Not only may this permit appropriate actions to avoid the pathogenic potential of these antibodies, but the detection serves in itself as a sensitive measure of ongoing oxidative damage. Thus, the detection of such antibodies may be used as the basis for modifying or terminating certain therapies or avoiding certain exposure risks.

Furthermore, in the development of new chemotherapeutic or radiotherapeutic agents or regimens with decreased side effects, it is useful to be able to assess oxidative damage in vivo. The compositions and methods of the present invention are therefore useful as screening tools in preclinical or clinical trials. They may be used to screen any agent capable of causing oxidative DNA damage by detecting the production of antibodies specific for an oxidized DNA base as a sensitive monitor of the occurrence of oxidative damage in vivo.

Having now generally described the invention, the same will be more readily understood through reference to the following examples which are provided by way of illustration, and are not intended to be limiting of the present invention, unless specified.

EXAMPLE I

Antigen Preparation and Assay System

Serum samples were obtained from patients tested for the presence of antinuclear antibodies (ANA), known to be associated with SLE, and from healthy people (normal sera, NS). These sera were tested for the presence of antibodies that recognize 5-hydroxymethyl uracil (HMU), one of the chemically stable oxidized DNA bases (Frenkel, 1989, supra; G. W. Teebor et al., *Proc. Natl. Acad. Sci. USA* 81, 318 (1984); K. Frenkel et al., *Biochemistry* 24, 4527 (1985)).

ELISA was used as the assay system. Antigen was prepared by periodate coupling of HMU riboside to bovine serum albumin (BSA), according to the method of B. F. Erlanger et al., Proc. Natl, Acad. Sci. 52:68 (1964), and followed by reduction with borohydride. This procedure led to the formation of a conjugate of HMU 2'-deoxyribonucleoside (HMdU) with lysine residues of BSA. The conjugate is designated herein HMdU-BSA. For comparison, conjugates in which thymine riboside was coupled to BSA (dT-BSA) were prepared. In addition, "mock coupled" bovine serum albumin (M-BSA) was also prepared. The crude products were desalted on a DG-P6 column (BioRad) and lyophilized. From the UV spectra of HMdU-BSA, BSA and HMdU, it was determined that 30–33 HMU residues were present in each HMdU-BSA.

Ninety six-well plates were pre-coated with HMdU-BSA, dT-BSA or M-BSA by incubating with 0.5–20 µg antigen/ml, pH 9.7, at 4° C. overnight. Additional blocking with BSA did not change the results. Plates were incubated with 200 µl of the appropriately diluted test sera at 37° C. for 2 h and washed 3 times with 0.05% Tween-PBS.

The wells were treated with 1:1000 dilution of goat anti-human IgG, IgA or IgM (abbreviated as anti-hIg antibodies), obtained from Sigma Chemical Co. (St. Louis, Mo.). The antibodies were conjugated with the enzyme, horseradish peroxidase (HRPO). After adding the labeled antibody, wells were again washed 3 times. The chromogenic substrate, o-phenylenediamine was used for $H_2O_2$ oxidation mediated by HRPO bound to the wells through the anti-human Ig antibodies. The color reaction, measured as absorbance at 490 nm ($A_{490}$) at acid pH in an ELISA-5 Microplate Reader (Physica Inc.) was proportional to the amount of human antibodies bound to the coated plates.

Optimal results were obtained when incubations with anti-human Ig antibodies and with the substrate were 1 h each. Assays were carried out on 2–4 replicate wells and each experimental point was determined 2–6 times. The results are expressed as absorbance at 490 nm ($A_{490}$) and, where applicable, mean $A_{490}$ ±SEM.

EXAMPLE II

HMdU is Recognized by Antibodies present in ANA-Positive Sera

Figure 8:
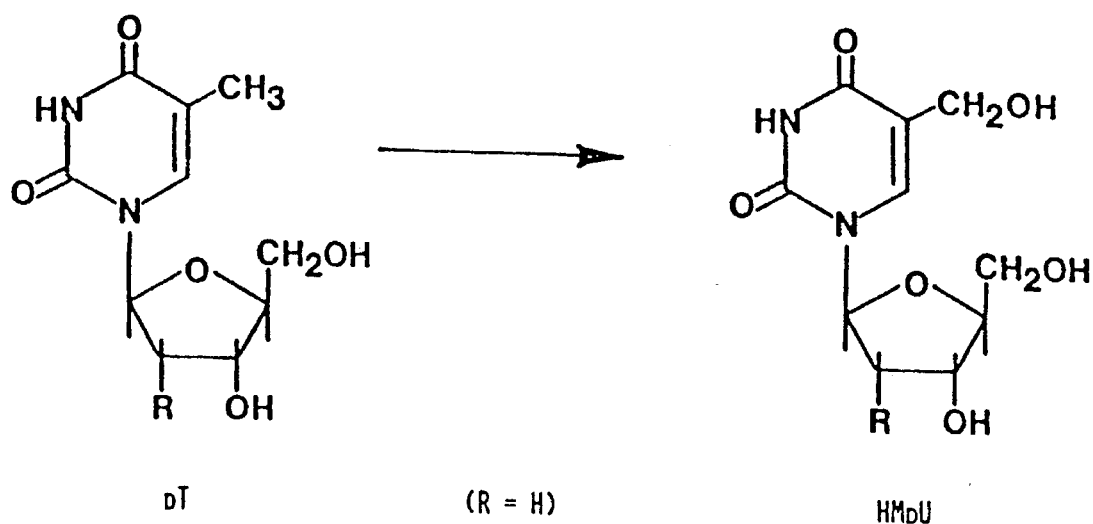
FIG. 8 shows the chemical structures of thymidine (dT) (left) and 5-hydroxymethyl-2'-deoxyuridine (HMdU) (right). In free (2'-deoxribonucleoside) form, the substituent labeled as R is hydrogen. When conjugated to the lysine residues of bovine serum albumin (BSA), R represents the BSA protein.

The structures of thymidine and its oxidation product HMdU are shown in FIG. 8. These moieties, when coupled to BSA and coated onto wells, provided the antigens in assays for the presence of antibodies in human sera.

HMdU was found to be recognized by antibodies present in patients' sera. However, of the three goat anti-hIg antibodies, only anti-IgM reacted with HMdU-bound human antibodies (FIG. 1B). As shown in FIG. 1C, anti-human IgG had only marginal binding. The anti-IgA was totally ineffective. These results indicated that the antibodies recognizing HMdU are of the IgM isotype.

Very little non-specific binding of anti-IgM occurred, as only a small amount was bound to the control M-BSA-coated wells (FIG. 1A). The goat anti-hIg antibodies used in this study were not affinity purified. Similar antibodies that had been affinity purified had only about 10% activity in this system. It is interesting to note that the monoclonal antibody generated against HMdU by the present inventors was also of the IgM isotype.

To prove that it is indeed the antigenic determinant of HMdU that is recognized by the serum antibodies being tested, serum samples were preincubated with soluble HMdU-BSA (800 μg/ml) at 37° C. for 1 h prior to incubation with the antigens bound to the wells. FIG. 1 shows that most of the anti-HMdU activity present in the serum was removed by the soluble HMdU-BSA, leaving only a small fraction to interact with the solid phase antigen.

Figure 2:
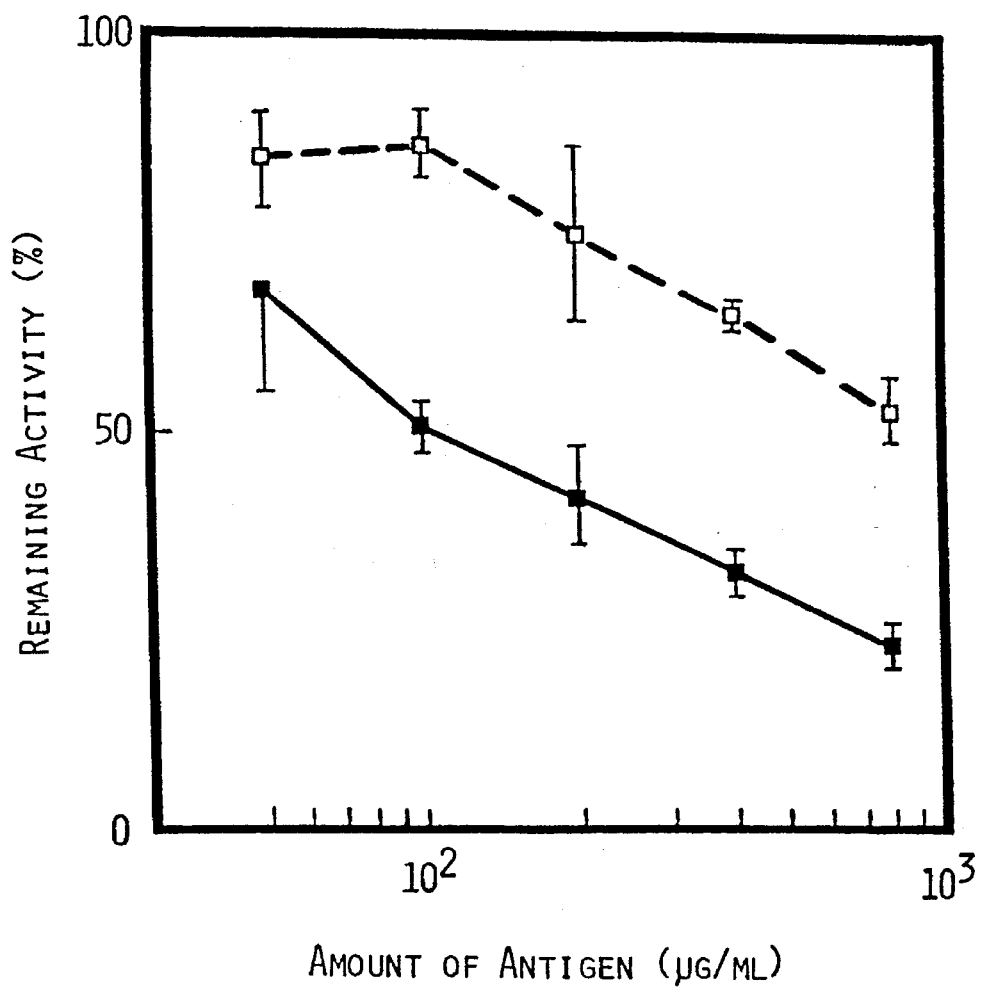
FIG. 2 is a graph showing the effect of HMdU-BSA pre-treatment on binding of antibodies present in ANA$^+$ sera of patient with lupus and collagen vascular disease to wells coated with HMdU-BSA, as determined by ELISA. Sera (2.5K dilution; 1 ml) were pre-treated with 50–800 µg HMdU-BSA (■) or free HMdU (□) at 4° C. overnight, then incubated with HMdU-BSA- and dT-BSA-coated plates, followed by goat anti-human IgM and the substrate. Results are expressed as mean values of percent of remaining antibody activity ± SEM, measured as $A_{490}$.

The inhibition of binding to wells coated with HMdU-BSA or dT-BSA was proportional to the amount of soluble HMdU-BSA (50–800 μg/ml) added to the pre-incubation mixture (with ANA$^+$sera) (FIG. 2). The effect was much greater on binding to HMdU-BSA-coated wells compared to dT-BSA-coated wells (See FIG. 3). Although ANA$^+$sera also bound to the dT-BSA-coated wells, pre-incubation of sera with the same amount of HMdU-BSA, dT-BSA or a mixture of both caused a proportionately greater decrease in binding to HMdU-BSA than to dT-BSA.

These results show that common antigenic determinants are present in HMdU and dT, which is not surprising considering the similarity of their structures (FIG. 8). The results also show that the serum antibodies have a greater specificity for HMdU.

To inhibit binding to coated wells, HMdU had to be coupled to BSA; free HMdU had very little if any activity (FIG. 2). These results suggest that the epitopes recognized by the antibodies present in ANA$^+$sera comprise more than a single HMdU residue and that the HMdU residues must assume a certain spatial distribution to become a recognizable epitope.

EXAMPLE III

Figure 4:
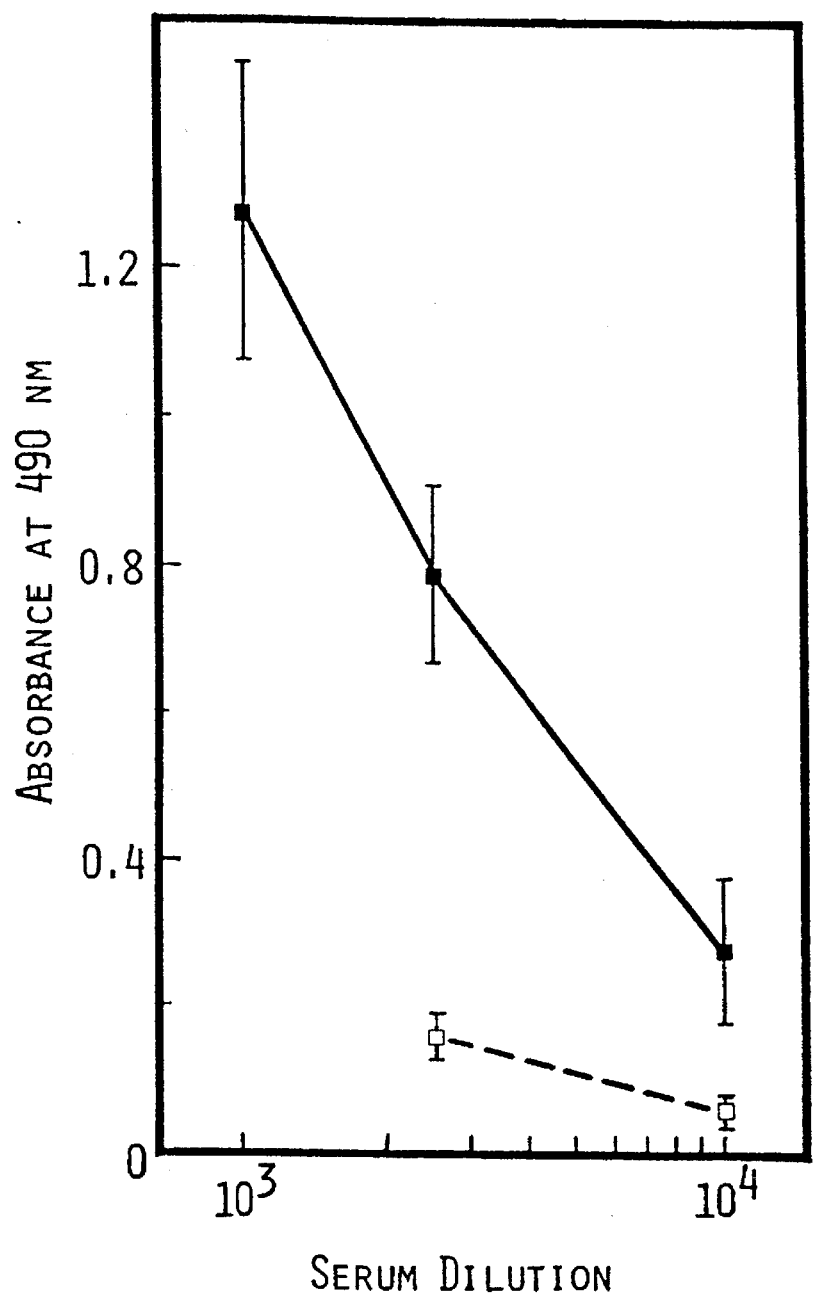
FIG. 4 is a graph showing the effects of concentration of ANA$^+$ sera on specific and non-specific binding to HMdU-BSA- and M-BSA-coated plates, respectively. Serum samples diluted 1K, 2.5K and 10K were applied to wells coated either with HMdU-BSA [N=15](■) or M-BSA [N=12](D), incubated, and goat anti-human IgM was added. Results are expressed as mean $A_{490}$ ± SEM of 2–4 experiments on each of the 12–15 sera tested in duplicate.
Figure 5:
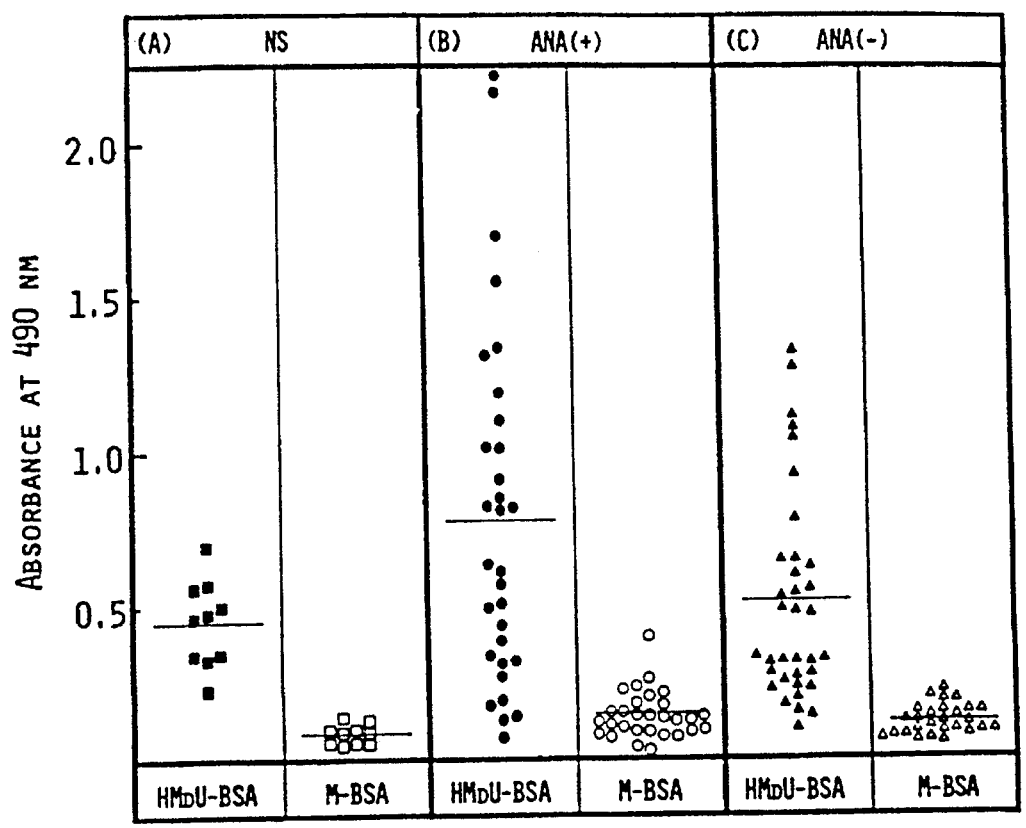
FIG. 5 is a graph showing specific and nonspecific binding of three different types of human sera (ANA$^+$, ANA$^-$ and NS) to plates coated with PIMdU-BSA and M-BSA, respectively, as determined by ELISA. Samples of ANA$^+$[N=35], ANN$^{-[N=}$32]and NS [N=10]sera were diluted 2.5K and incubated with HMdU-BSA- and M-BSA-coated wells as above, followed by anti-human IgM and the substrate. Results are expressed as mean $A_{490}$ values of 2–6 experiments, each in 2–4 replicate wells. Panel A shows the results with NS; Panel B shows results with ANA$^+$ sera; Panel C shows results with ANA$^-$ sera. Filled symbols represent specific binding. Open symbols represent non-specific binding.

Comparison of Binding of Antibodies in ANA-Positive, ANA-Negative and Normal Sera to HMdU-BSA The binding of antibodies to immobilized antigens was proportional to the concentration of ANA$^+$sera at dilutions between $10^{-3}$ and $10^{-4}$ (FIG. 4), and to the amount of HMdU-BSA used to coat the wells. Only a small proportion of the total binding activity could be attributed to non-specific interactions, as shown by assays with M-BSA-coated wells (FIG. 5). Based on these results, dilutions of 1:2,500 (2.5K) were used in the other experiments.

The sensitivity of this assay exceeds that of the indirect immunofluorometric ANA determination (J.-C. Bystryn, Supra) by 15–125 times. More importantly, this assay is more sensitive than an assay using oxidized ds DNA (S. Blount et al., supra) by 25–50 fold.

The distribution of specific (HMdU-BSA) and non-specific (M-BSA) binding of various ANA$^+$, ANA$^-$ and normal (NS) sera is shown in FIG. 5. The scatter in binding may be associated with varying severity of the disease in ANA$^+$ patients (FIG. 5A) or may be due to the varying presence of some inflammatory conditions among ANA$^-$patients (FIG. 5B). Table 1, below, summarizes these results. It is clear that binding of ANA$^+$sera to HMdU-BSA was significantly higher ($p<0.05$) than binding of ANA$^-$sera, and still higher than NS ($p<0.005$), as determined by Student's t test. Binding of ANA$^-$sera was not significantly different from binding of NS ($p=0.5$). Subtracting appropriate nonspecific binding and NS values from those of ANA$^+$ and ANA$^-$ shows the magnitude of the difference in recognition of HMdU-BSA antigen between ANA$^+$ and ANA$^-$ sera.

TABLE 1

ELISA Assay of Reactivity of ANA$^+$ and ANA$^-$ Sera with an Oxidized Base (HMdU-BSA)

| | HMdU-BSA | | M-BSA | |
|---|---|---|---|---|
| Sera | N | Mean $A_{490}$ (± SEM) | N | Mean $A_{490}$ (± SEM) |
| ANA$^+$ | 32 | 0.783$^a$ ± 0.100 | 30 | 0.146 ± 0.014 |
| ANA$^-$ | 35 | 0.503$^b$ ± 0.057 | 27 | 0.120 ± 0.008 |
| NS | 10 | 0.452 ± 0.045 | 10 | 0.085 ± 0.010 |

Samples were assayed 2–6 times with 2–4 replicate wells each. Means and standard errors of the mean are shown.
Significance of differences between groups was determined by Student's t test.
$^a$Significantly different from ANA$^-$ ($p < 0.05$) and from NS ($p < 0.005$).
$^b$Not significantly different from NS ($p = 0.5$).

EXAMPLE IV

Correlation of Anti HMdU-BSA Antibody Activity with Inflammatory Conditions

Figure 6:
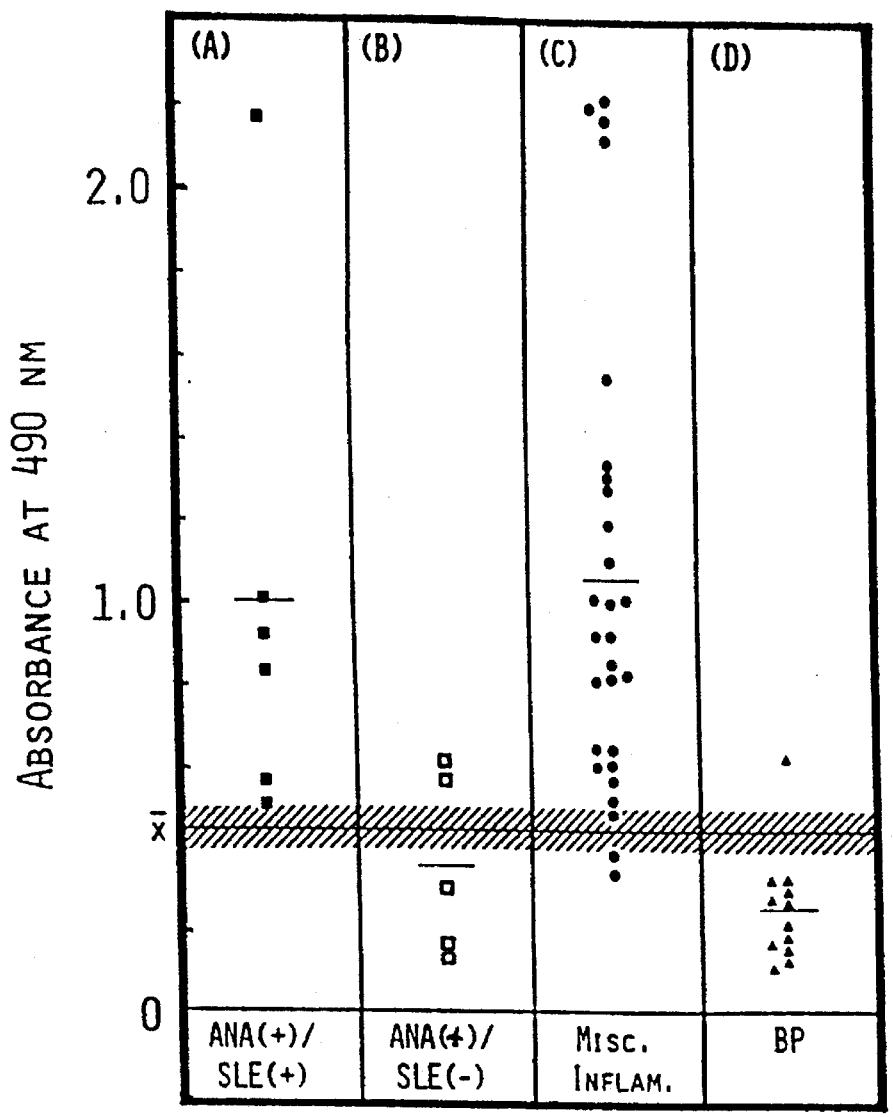
FIG. 6 is a graph showing the specific binding of patients' sera to HMdU-BSA-coated wells; Panel A represents confirmed SLE (ANA$^+$/SLE$^+$). Panel B represents other ANA$^+$ patients in whom SLE was not confirmed (ANA$^+$/SLE$^-$) Panel C represents miscellaneous inflammatory autoimmune diseases. Panel D represents patients with bullous pemphigoid (BP). The dotted area shows the range of the mean ±SEM of NS binding to HMdU-BSA (taken from Table 1).

Upon replotting some of the data obtained above in relation to the actual clinical diagnoses of the patients, the scattergrams shown in FIG. 6 were obtained. The results obtained with the present ELISA method correlated much better with presence of any inflammatory disease. The diseases in this group included SLE, discoid lupus, drug-induced lupus, collagen vascular disease, and CREST, all autoimmune conditions (S. Blount et al., lg30 supra; B. D. Stollar, supra; A. J. G. Swaak et al., supra; E. M. Tan et al., supra; T. Swaak et al., supra D. S. Pisetsky et al., supra; J.-C. Bystryn, supra).

Figure 7:
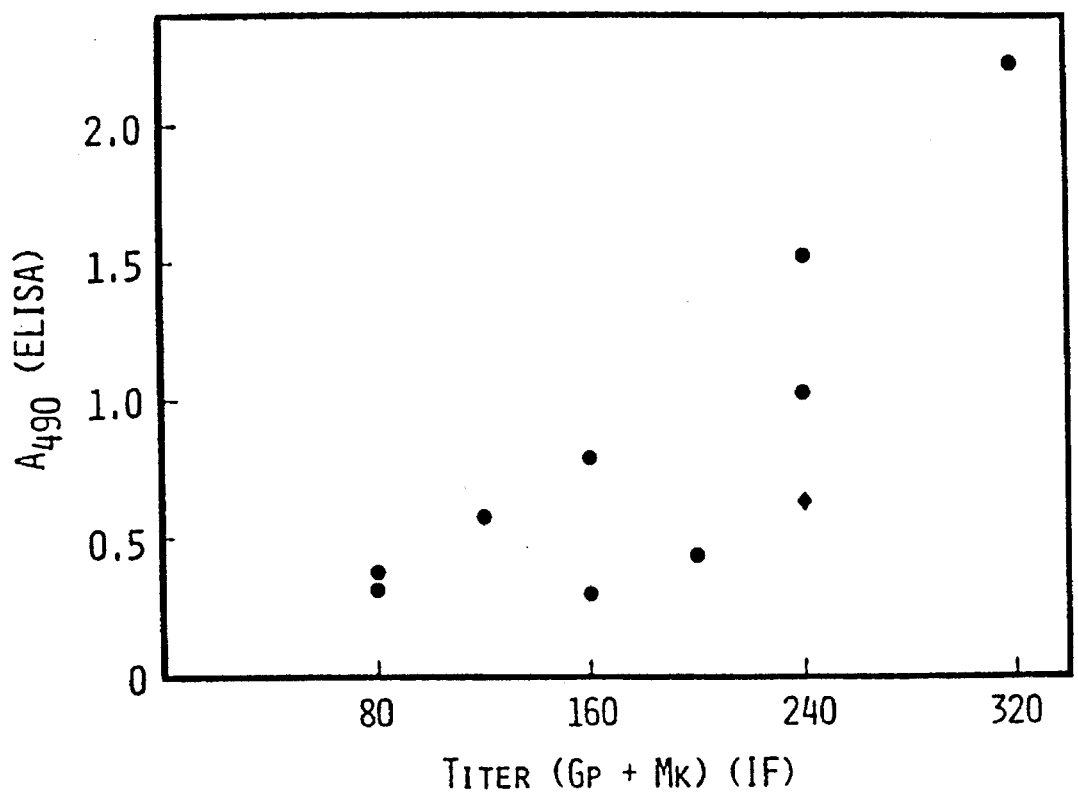
FIG. 7 is a graph comparing the results obtained by ELISA (as described above) with those obtained using indirect immunofluorescence (IIF) analyses of sera containing antibodies against intracellular (IC) deposits (●) [N=9] and basement membrane zone (BMZ) (♦) [N=1]. Each serum (2.5K dilution) was analyzed 3–4 times by ELISA, using 2–4 replicate wells. Results are expressed as mean $A_{490}$ values (ELISA) vs. combined serum titer against monkey and guinea pig esophagi (IIF).

Binding of sera of patients with confirmed SLE (ANA$^+$/SLE$^+$) was significantly higher ($p<0.05$) than the mean value for the control NS group (FIG. 6A). However, binding levels of ANA$^+$ sera of patients without active SLE (ANA$^+$/SLE$^-$) were not different from the mean of the NS group (FIG. 6B). Sera of patients suffering from various inflammatory conditions (including SLE) showed the greatest mean binding to HMdU-BSA (p<0.001); the majority of wells were above the mean of the NS group and only a few were within the normal range (FIG. 6C). Interestingly, binding values of sera of patients with bullous pemphigoid (BP) disease were scattered well below those of the normal controls, except a single value. This particular patient also showed deposits in the basement membrane zone (BMZ), as determined by IIF (Bystryn, supra). The decline below NS means was significant (p<0.005). Table 2 summarizes these results. The assay method of the present invention provided results that correlated well with IIF also in determination of intercellular (IC) deposits (FIG. 7), when the results of ELISA are plotted vs the dilution of sera required for binding to monkey and guinea pig esophagi in the IIF assay. Values for the BMZ fell together with those of IC.

TABLE 2

Antibodies to HMdU-BSA in Sera of Patients with (ANA$^+$/SLE$^+$) or without (ANA$^+$/SLE$^-$) Clinically-Confirmed SLE, Miscellaneous Inflammatory Autoimmune Diseases and Bullous Pemphigoid (BP)

| Patient Change[b] | N | Mean A$_{490}$ (± SEM) | Significance[a] | |
|---|---|---|---|---|
| ANA$^+$/SLE$^+$ | 6 | 1.002 ± 0.247 | p < 0.05 | ↑ |
| ANA$^+$/SLE$^-$ | 5 | 0.360 ± 0.099 | ns[c] | — |
| Misc. Inflam. | 28 | 1.060 ± 0.107 | p < 0.001 | ↑ |
| BP | 12 | 0.260 ± 0.039 | p < 0.005 | ↓ |

[a]Significance, compared to normal human sera, (NS), was determined by Student's t test. Results for NS are given in Table 1.
[b]Increase or decrease compared to NS.
[c]ns - not significant.

EXAMPLE V

General Discussion and Possible Protective Role of Antibodies to Oxidized Bases

Use of the assay of the present invention shows that sera of patients with active inflammatory autoimmune diseases contain antibodies that recognize specific oxidized DNA bases, as exemplified by HMU. These results point to the following sequence of events. Oxidative stress caused by inflammatory processes induces production of oxidants by infiltrating phagocytic cells. This in turn causes strand breaks, oxidative modification of DNA bases and the release of the DNA fragments containing the oxidized bases. Such DNA fragments elicit an immune response that results in production of antibodies that recognize oxidized bases such as HMU and probably others as well. Hence, appearance of these antibodies in sera serve as a measure of inflammation in autoimmune diseases. Measurement of these antibodies, according to the present invention, is useful in monitoring the progression and abatement of such inflammatory states.

Sera from healthy human donors also contain detectable levels of antibodies that bind to HMdU-BSA (group NS in FIG. 5). Such antibodies are presumably normal, and may subserve a protective role from damage caused by the ongoing basal oxidative processes that are constantly occurring in the body. Such antibodies would provide an additional line of defense against oxidative DNA damage, after the repair enzymes which remove oxidized bases or excise damaged DNA fragments (reviewed in G. W. Teebor et al., Adv. Cancer Res. 38, 23 (1983); Int, J. Radiation Biol., supra).

The oxidized bases 5-hydroxymethyl uracil, thymine glycol and 8-hydroxyguanine, and some of their nucleosides, are known to be excreted in urine by humans and animals (R. L. Saul et al., in: Mechanism of DNA Damage and Repair, M. G. Simic et al., Eds., Plenum Publishing Corp., New York, N.Y., 1986, pp. 529–535; K. C. Cundy et al., in: Oxygen Radicals in Biology and Medicine, M. G. Simic et al., Eds., Plenum Publishing Corp., New York, N.Y., 1988, pp. 479–482.). When the oxidative insult occurring during inflammatory conditions cannot be properly counteracted by the cellular antioxidant and repair processes (S. H. Khan et al., Free Rad. Biol. Med. 8, 339 (1990)), production of antibodies specific for oxidized DNA base antibodies appears to be enhanced. Increases in the levels of these circulating antibodies could lead to enhanced formation of immune complexes with DNA, and the deposition and precipitation of the complexes in renal glomeruli. The precipitates could stimulate further immune responses leading to the cascading formation of antibodies reactive with oxidatively damaged DNA. This process would serve as the pathophysiological basis of the autoimmune response occurring in SLE and other related disorders.

EXAMPLE VI

Enhanced Titers of Atibodes to an Oxidized DNA Base in Inflammatory and Neoplastic Diseases A total of 97 subjects were enrolled in this study. Of these, 13 were normal controls, 18 had psoriasis, 7 had immune complex disease, 22 had neoplastic disease or a history of neoplasia, and 10 had venous leg ulcers. None or these patients were receiving systemic cytotoxic or antiinflammatory therapy. Twenty patients with psoriasis who were getting concomitant cytotoxic or antiinflammatory therapy were assigned to a separate group. The remainder of the subjects did not fit into any of the above groups because of multiple cutaneous problems or because they had a dermatologic problem such as ache, rosacea or dermatophytosis, which did not fit into any of the above categories. The number of such patients was too low for separate categorization.

The immune complex diseases represented in the above patient population included leukocytoclastic vasculitis, urticarial vasculitis, Raynaud's disease as well as SLE. The neoplastic disease group included patients with a history of a benign or malignant neoplasms of the cutaneous, female reproductive or respiratory systems, or were so diagnosed upon examination for another complaint.

HMdU or dT was coupled to BSA as described above, and ELISA assays performed according to the procedure detailed above. The results are shown in Table 3. Anti-HMdU antibody titers were markedly elevated in patients with psoriasis, immune complex disease or a history of neoplasia. The reactivity of sera from patients undergoing systemic treatment with antiinflammatory or cytotoxic drug, including prednisone, methotrexate, plaquenil, etretinate and dapsone, was significantly decreased compared to patients not receiving systemic therapy. Antibody titers of patients with venous leg ulcers were significantly lower than controls.

TABLE 3

Detection of Anti-HMdU Antibodies in Human Sera by ELISA

| Group Significance[2] | N | Anti-HMdU Ab Titer Mean ± SEM[1] | Change from Control | |
|---|---|---|---|---|
| Controls | 13 | 14.9 ± 2.2 | | |
| Psoriasis | 18 | 24.6 ± 4.6 | up | p < 0.001 |

TABLE 3-continued

Detection of Anti-HMdU Antibodies in Human Sera by ELISA

| Group Significance[2] | N | Anti-HMdU Ab Titer Mean ± SEM[1] | Change from Control | |
|---|---|---|---|---|
| Neoplastic Diseases | 11 | 46.4 ± 7.5 | up | p < 0.001 |
| Immune Complexes | 7 | 42.9 ± 11.8 | up | p < 0.001 |
| Venous Leg Ulcers | 10 | 11.0 ± 2.3 | down | p < 0.02 |
| Systemically-treated Inflammatory Dermatoses | 20 | 17.3 ± 2.7[3] | up | ns[4] |

Figure 9:
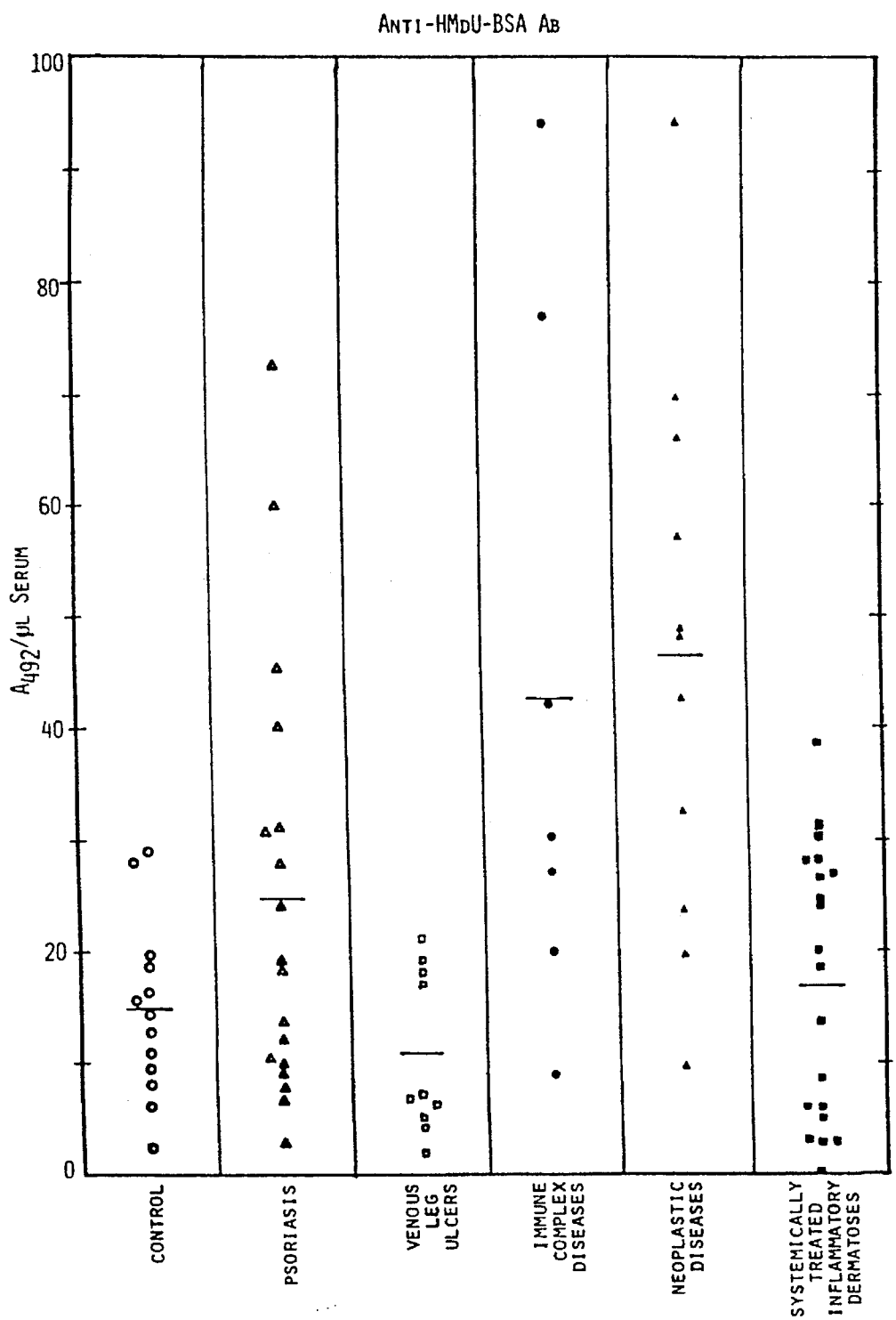
FIG. 9 is a scattergram of the mean values of anti-HMdU antibodies ($A_{492}$/µl serum) present in human sera categorized according to disease type.

[1]Values shown represent the mean (± standard error of the mean) absorbance at 492 nm per μl serum.
[2]The statistical significance of the results (relative to controls) was evaluated using Student's t test. P values of 0.05 or less are considered significant.
[3]Significantly lower than antibody titers in patients with psoriasis (p < 0.001), neoplastic diseases (p < 0.005) and immune complex disease (p < 0.001).
[4]ns = not significant The scattergram in FIG. 9 shows the distribution of the actual absorbance mean values/μl of sera calculated for the individual patients. The venous leg ulcer group is contained within the absorbance distribution of the controls, while the drug treated group has only a few individual values above control levels. More than half of the values in the psoriasis group (11 of 18) were above the control mean. In groups of patients with immune complex diseases or a history of neoplasia, only one point in each group fell below the control mean. Sera of over 85% of the individuals had anti-HMdU antibody titers above the mean control value.

Figure 3:
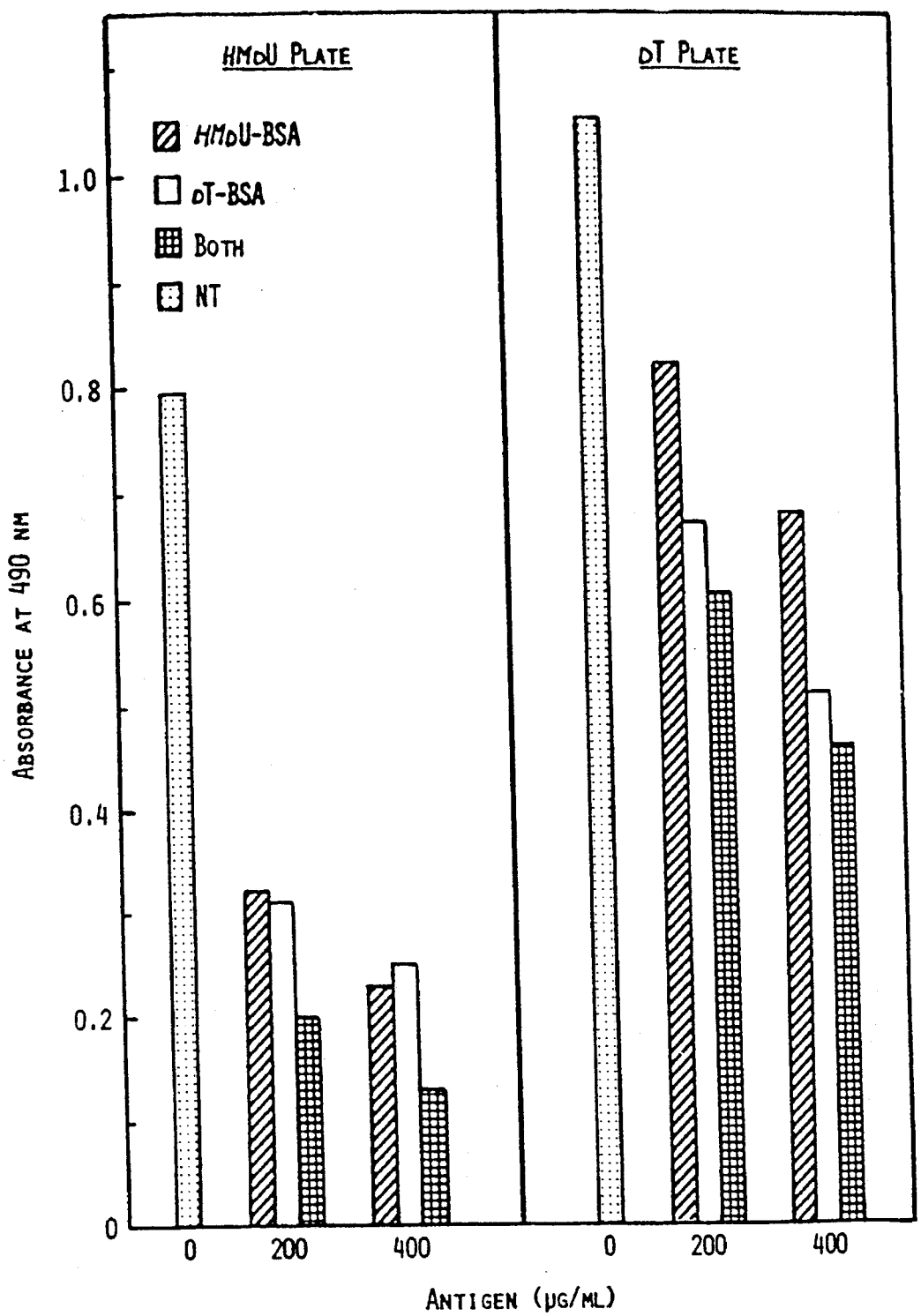
FIG. 3 is a graph showing the effect of pretreating ANA$^+$ serum with HMdU-BSA and dT-BSA on the binding of antibodies to HMdU or dT. ANA$^+$ serum (#27; diluted 1:2,500; 1 ml) was incubated overnight at 4° C. in the absence (NT) or presence of 200 µg or 400 µg of either HMdU-BSA, dT-BSA or a mixture of both. This preincubated serum was then tested for binding to microplates coated with either HMdU-BSA or dT-BSA.
Figure 10:
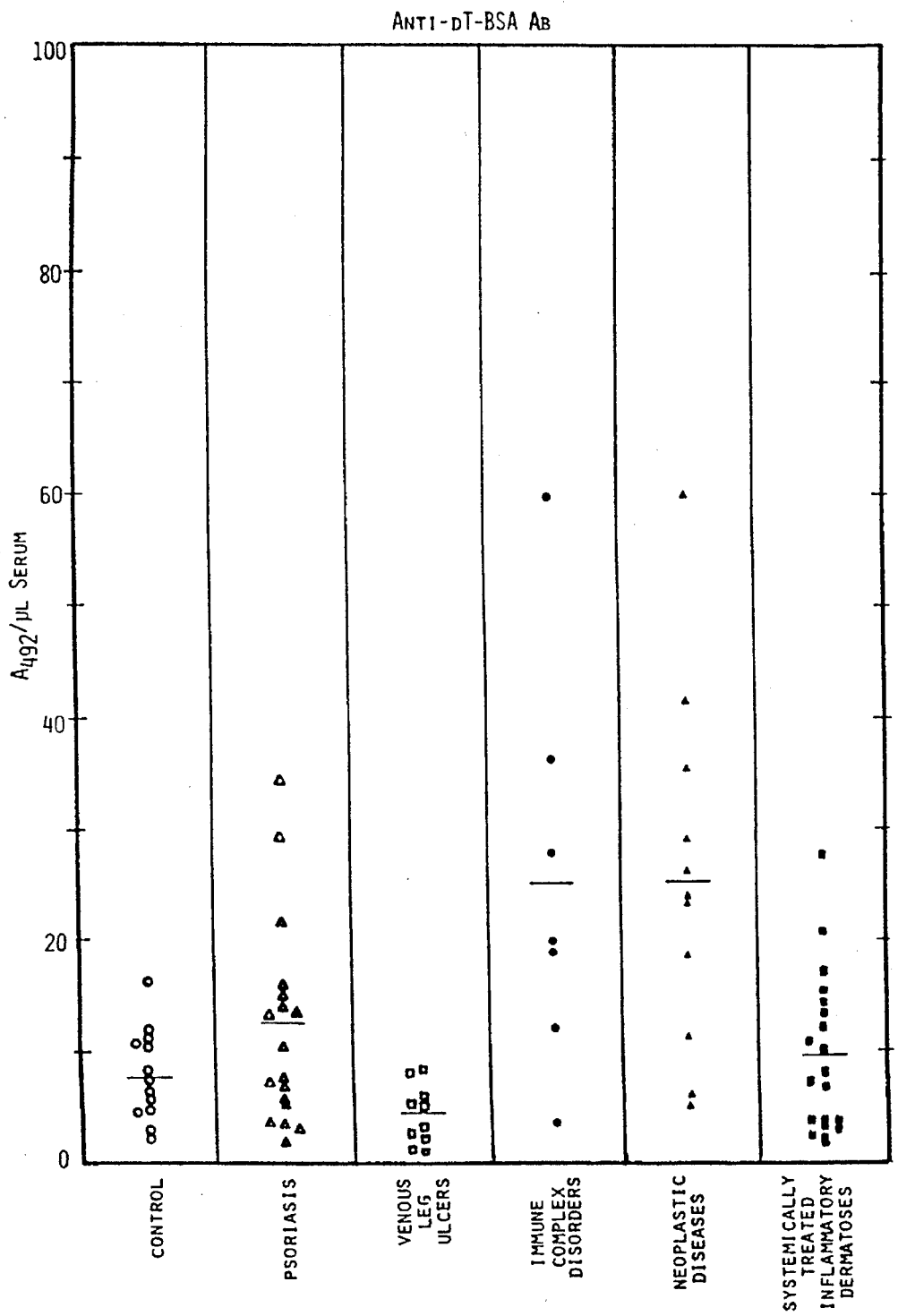
FIG. 10 is a scattergram of the mean values of anti-dT antibodies ($A_{492}$/µl serum) present in human sera categorized according to disease type, analyzed at the same time as anti-HMdU antibodies, as shown in FIG. 9.

FIG. 10 shows a scattergram of the individual mean values of sera incubated in dT-BSA-coated wells. A comparison of the values listed in Tables 3 and 4 shows that avidties of antibody binding to dT-BSA (FIG. 10) are on average two-fold lower than those binding to HMdU-BSA (FIG. 9). As discussed earlier, even when a patient's serum binds somewhat more avidly to dT-BSA, pretreatment of serum with HMdU-BSA, dT-BSA, or a mixture of the two, binding to HMdU-coated wells was decreased more markedly than binding to dT-coated wells (FIG. 3).

TABLE 4

Detection of Anti-dT Antibodies in Human Sera by ELISA

| Group | N | Anti-dT Ab Titer Mean ± SEM[1] | Change from Control | Significance[2] |
|---|---|---|---|---|
| Controls | 13 | 7.7 ± 1.1 | | |
| Psoriasis | 18 | 12.1 ± 2.1 | up | p < 0.001 |
| Neoplastic Diseases | 11 | 24.4 ± 7.0 | up | p < 0.001 |
| Immune Complexes | 7 | 25.4 ± 6.9 | up | p < 0.005 |
| Venous Leg Ulcers | 10 | 4.2 ± 0.8 | down | p < 0.01 |
| Systemically-treated Inflammatory Dermatoses | 20 | 9.4 ± 1.6[3] | up | p < 0.05 |

[1]Values shown represent the mean (± standard error of the mean) absorbance at 492 nm per μl serum.
[2]The statistical significance of the results (relative to controls) was evaluated using Student's t test. P values of 0.05 or less are considered significant.
[3]Significantly lower than antibody titers in patients with psoriasis (p < 0.05), neoplastic diseases (p < 0.001) and immune complex disease (p < 0.005).

The results presented herein show that all people elaborate antibodies that bind to HMdU-BSA and with less avidity to dT-BSA. However, the levels of these antibodies in serum varies significantly with the health of the individual. Patients with inflammatory diseases produce higher amounts of these antibodies, and treatment with systemically administered medication can markedly lower the anti-HMdU and anti-dT titers.

Patients with venous leg ulcers, an older group of people with minimal or no cutaneous inflammation had significantly lower antibody titers than did healthy controls, for reasons not yet clear. This result may be related to the overall fall in humoral immunity with advanced age.

The large variation in anti-HMdU titers in psoriasis patients may reflect the state of the disease process, such as whether it was stable, improving or flaring. The percentage of body surface covered with lesions and/or the severity of the lesions likely modulate the immune response, thereby affecting the anti-HMdU titers.

The reasons for production of the antibodies specific for oxidized DNA bases are not known. Reactive oxygen species produced in the various pathophysiological processes can oxidize DNA bases in phagocytic cells or their neighboring cells. In attempting to repair this damaged DNA, repair enzymes may release segments of DNA containing oxidized bases, which then act as antigenic determinants evoking an antibody response. Complexes of antibody with oxidatively damaged DNA may circulate before elimination, which could augment the inflammatory response. Regardless of the precise mechanism involved in stimulating the antibody response to oxidized DNA bases, the presence of the antibodies can be exploited as a diagnostic tool, and used to monitor patients' responses to medical and surgical therapies.

The references cited above are all entirely incorporated by reference herein, whether specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

What is claimed is:

1. A composition useful for detecting or measuring antibodies specific for an oxidized DNA base, consisting essentially of a solid phase support having immobilized thereon an antigen consisting of a molecule including an oxidized DNA base which is not part of an oligonucleotide or polynucleotide molecule.

2. A composition according to claim 1, wherein said antigen is covalently linked to a protein which is immobilized on said support.

3. A composition according to claim 2, wherein said protein is selected from bovine serum albumin, ovalbumin, human serum albumin and milk protein.

4. A composition according to claim 1, wherein said oxidized DNA base is selected from the group consisting of 5-hydroxymethyl uracil, thymine glycol and 8-hydroxyguanine.

5. A composition according to claim 4, wherein said oxidized DNA base is 5-hydroxymethyl uracil.

6. A composition according to claim 1 wherein said support is selected from the group consisting of glass, polystyrene, polypropylene, polyethylene, dextran, nylon, amylases, natural and modified celluloses, polyacrylamide, agarose, and magnetite.

7. A composition according to claim 6, wherein said support is polystyrene.

8. A composition according to claim 7, wherein said polystyrene is in the form of a microtiter plate.

9. An immunoassay method for detecting antibodies specific for an oxidized DNA base, comprising:
   (a) contacting a sample suspected of containing said antibodies with a composition according to claim 1;
   (b) allowing any of said antibodies to bind to said oxidized DNA base;
   (c) adding a detectably labeled binding partner for said antibodies to said bound antibodies and allowing said binding partner to bind to said antibodies; and
   (d) measuring the amount of bound or unbound labeled binding partner,
thereby detecting said antibodies.

10. A method according to claim 9, wherein said support is selected from the group consisting of glass, polystyrene, polypropylene, polyethylene, dextran, nylon, amylases, natural and modified celluloses, polyacrylamide, agarose, and magnetite.

11. A method according to claim 9, wherein said binding partner is (a) an antibody specific for a human immunoglobulin or (b) a bacterial protein capable of binding to a human immunoglobulin molecule.

12. A method according to claim 9, wherein said antigen is covalently linked to a protein which is immobilized on said support.

13. A method for diagnosing in a subject a disease or condition the pathogenesis of which includes oxidative damage to DNA, comprising:
   obtaining from said subject a sample of a biological fluid; and
   detecting, in said sample, antibodies specific for an oxidized DNA base using an immunoassay method in accordance with claim 9,
   wherein the presence of said antibodies at a concentration above normal concentration indicates that said disease or condition exists.

14. A method for monitoring the progression or the regression in a subject of a disease or condition the pathogenesis of which includes oxidative damage to DNA, comprising:
   obtaining from said subject on at least two occasions separated in time by at least about seven days, at least a first and a second sample of a biological fluid; and
   detecting, in each said sample, antibodies specific for an oxidized DNA base using an immunoassay method in accordance with claim 9,
   wherein an increase in the concentration of said antibodies from an earlier to a later sample is associated with a progression of said disease or condition and wherein a decrease in the concentration of said antibodies from an earlier to a later sample is associated with a regression of said disease or condition.

15. A composition in accordance with claim 11, wherein said antigen is 5-hydroxymethyl-2'-deoxyuridine.

16. An immunoassay method for detecting antibodies specific for an oxidized DNA base, comprising
   (a) contacting a sample suspected of containing said antibodies with an oxidized DNA base which is not part of an oligonucleotide or polynucleotide molecule; and
   (b) measuring the amount of antibodies in said sample which are specific for said base.

17. A method according to claim 16, wherein said oxidized DNA base is selected from the group consisting of 5-hydroxymethyl uracil, thymine glycol and 8-hydroxyguanine.

18. A method for diagnosing in a subject a disease or condition the pathogenesis of which includes oxidative damage to DNA, comprising:
   obtaining from said subject a sample of a biological fluid; and
   detecting, in said sample, antibodies specific for an oxidized DNA base using an immunoassay method in accordance with claim 16,
   wherein the presence of said antibodies at a concentration above normal concentration indicates that said disease or condition exists.

19. A method for monitoring the progression or the regression in a subject of a disease or condition the pathogenesis of which includes oxidative damage to DNA, comprising:
   obtaining from said subject on at least two occasions separated in time by at least about seven days, at least a first and a second sample of a biological fluid; and
   detecting, in each said sample, antibodies specific for an oxidized DNA base using an immunoassay method in accordance with claim 16,
   wherein an increase in the concentration of said antibodies from an earlier to a later sample is associated with a progression of said disease or condition and wherein a decrease in the concentration of said antibodies from an earlier to a later sample is associated with a regression of said disease or condition.

20. A kit for detecting antibodies for an oxidized DNA base, said kit being compartmentalized to receive in close confinement therein one or more containers, said kit comprising:
   a first container containing an antigen immobilized on or capable of being immobilized on a solid phase support, said antigen consisting of a molecule including an oxidized DNA base which is not part of an oligonucleotide or polynucleotide molecule; and
   a second container containing a detectably labeled binding partner for the antibodies to be detected.

21. A kit according to claim 20, wherein said antigen is immobilized on a solid phase support.

22. A kit according to claim 20, additionally comprising:
   a third container containing an agent capable of reacting with said detectably labeled binding partner to yield a detectable reaction product.

23. A composition useful for detecting or measuring antibodies specific for an oxidized DNA base, consisting of a solid phase support having immobilized thereon an antigen consisting of a molecule including an oxidized DNA base which is not part of an oligonucleotide or polynucleotide molecule.

* * * * *